United States Patent [19]

Horn

[11] Patent Number: 5,773,973
[45] Date of Patent: Jun. 30, 1998

[54] METHOD OF MAGNETO OPTIC IMAGE FEATURE EXTRACTION

[75] Inventor: Michael Horn, South Setauket, N.Y.

[73] Assignee: Northrop Grumman Corporation, Los Angeles, Calif.

[21] Appl. No.: 622,128

[22] Filed: Mar. 26, 1996

[51] Int. Cl.⁶ .......................... G01N 27/82; G01N 21/21; G01R 33/032

[52] U.S. Cl. .......................... 324/235; 324/226; 324/228; 324/244.1; 324/262; 356/237

[58] Field of Search ..................................... 324/226, 228, 324/232–235, 238–242, 244.1, 260, 262, 263; 356/237; 382/145, 147, 149, 152, 181

[56] References Cited

U.S. PATENT DOCUMENTS

| | | | |
|---|---|---|---|
| 4,142,154 | 2/1979 | Couchman | 324/238 X |
| 4,379,261 | 4/1983 | Lakin | 324/232 X |
| 4,445,089 | 4/1984 | Harrison | 324/238 |
| 4,668,914 | 5/1987 | Kersten et al. | 324/251 |
| 5,053,704 | 10/1991 | Fitzpatrick | 324/238 X |
| 5,446,378 | 8/1995 | Reich et al. | 324/238 |
| 5,574,368 | 11/1996 | Horn et al. | 324/238 X |

Primary Examiner—Gerard R. Strecker
Attorney, Agent, or Firm—Terry J. Anderson; Karl J. Hoch, Jr.

[57] ABSTRACT

A method of magneto optic imaging to locate the presence of a crack around a circular drilled bolt hole wherein the circular bolt hole, because of its sharp corners, locally disturbs the magnetic field used to form the image and obscures the presence of a crack therearound. Initially, a magneto optic image is formed of the drilled circular bolt hole under test, wherein a crack near the circular hole will perturb the circularity of the hole image by driving the magnetic field away from the circumference of the circular hole to cause it to appear out of round and eccentric. A pattern recognition analysis is then applied to the image to check the image for circular shapes, wherein each circular shape image is correlated with a circle of similar diameter to check the circularity of the image, and an eccentricity of the circular image shape is indicative of a crack around the drilled circular bolt hole. In greater detail, a computer program, in a bit by bit comparison, looks for differences in the diameter of the hole image which can be related to eccentricity, which is characteristic of a crack around the circular hole.

11 Claims, 8 Drawing Sheets

METHOD OF MAGNETO OPTIC IMAGE FEATURE EXTRACTION

BACKGROUND OF THE INVENTION

1. Field of the Invention

The present invention relates generally to an area of non-destructive inspection technology known as magneto-optic/eddy-current imaging. More particularly, the subject invention pertains to a method of magneto optic image feature extraction wherein the circularity of a magneto optic image of a drilled bolt hole is correlated with a circle of similar diameter to check the image for eccentricity, which is indicative of the presence of a crack around the drilled bolt hole.

2. Discussion of the Prior Art

Magneto optic imaging is becoming a widely used tool to examine metallurgical structures for flaws and defects. In particular, the use of magneto optic imaging for locating cracks around bolt holes is of great value, particularly in structures such as an aircraft wherein the presence of a crack around a bolt hole can have dire consequences. However, even though magneto optic imaging forms an image of a crack, the image is not always easy to interpret. One reason for this difficulty is that a typical magneto optic imaging crystal such as Garnet has many irregularities which adversely affect the magnetic image as crazing across the entire image field. Another problem with interpreting the image is that a crack which is sought to be detected usually appears at the edge of a drilled bolt hole. The drilled bolt hole, because of its sharp 90° corners, causes a local disturbance in the magnetic field used for imaging and obscures the presence of a crack therearound. This problem can be addressed in several ways, including one which is the subject of U.S. Pat. No. 5,574,368, issued Nov. 12, 1996, the entire disclosure of which is hereby expressly incorporated by reference herein. Pursuant to the teachings of the present invention, this problem is solved by the application of image processing to the magneto optic image.

Drilled bolt holes are naturally round, and on aircraft structures are round to a high degree of precision. The magneto optic imaging system forms this same round shape when it images a drilled bolt hole under test. A crack around the edge of the drilled bolt hole will perturb the circularity of the hole image by driving the magnetic field away from the circumference of the drilled hole. This effect causes the magneto optic image of the drilled hole to appear out of round or eccentric. With the presence of a large crack around a drilled bolt hole, the out of round condition is easily detected visually. However when a crack around a drilled hole is very small, the perturbation in circularity is commensurately small and is very difficult to detect visually, and very often the crack is not detected at all.

SUMMARY OF THE INVENTION

Accordingly, it is a primary object of the present invention to provide a method of processing a magneto optic image to determine the presence of particular features therein.

A further object of the subject invention is to apply a pattern recognition analysis to a magneto optic image to solve the aforementioned detection problem. The image is scanned by a pattern recognition program which checks the image for circular image shapes. When a circular image shape is detected, it is compared with a circle of similar diameter, and the circularity of the image is determined. In a bit by bit comparison, the pattern recognition program looks for differences in the diameter of the image which can be related to an eccentricity, which in turn are characteristic of a crack around a circular drilled bolt hole. The pattern recognition computer program has a high sensitivity to the slight changes in the image caused by a small crack, thereby achieving a method for locating this phenomenon with relative ease.

In accordance with the teachings herein, the present invention provides a method of magneto optic imaging to locate the presence of a crack around a circular hole wherein the circular hole, because of its sharp corners, locally disturbs the magnetic field used to form the magneto optic image and obscures the presence of a crack therearound. A magneto optic image is formed of the circular hole under test, wherein a crack near the circular hole perturbs the circularity of the hole image by driving the magnetic field away from the circumference of the circular hole to cause the image of the hole to appear out of round and eccentric. A pattern recognition analysis is applied to the image to check the image for circular shapes, wherein each circular shape image is correlated with a circle of similar diameter to check the circularity of the image, and an eccentricity of the circular image shape is indicative of a crack around the circular hole.

In greater detail, a computer program, in a bit by bit comparison, looks for differences in the diameter of the hole image which can be related to eccentricity, which is characteristic of a crack around the circular hole.

The present invention provides a magneto-optic effect sensor capable of remote unmanned inspections, wherein normal magnetic fields caused by crack and corrosion induced disruptions of eddy currents in structure being inspected are optimized, thus reducing background interference effects in the sensor image. The subject invention provides an enhanced magneto-optically generated image which makes it possible to detect cracks and other defects not visible in conventional magneto-optic sensor images, and to perform the detection more rapidly than is possible with prior magneto-optic sensors. The present invention increases the signal-to-noise or image-to-background ratio of a magneto-optically generated image sufficiently to enable automatic detection methods using pattern recognition techniques to be employed, thus making possible completely unmanned monitoring of cracks and corrosion, and the use of miniaturized remotely operated eddy current detector robots.

BRIEF DESCRIPTION OF THE DRAWINGS

The foregoing objects and advantages of the present invention for a method of magneto optic image feature extraction may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Conventional magneto-optic/eddy current imaging technology has been used to generate real-time images of defects, such as fatigue, cracks and corrosion, in metals, and cracks, delamination and other defects in non-metallic structures. Instruments which utilize the Faraday magneto-optic effect, first discovered in 1845, operate by employing a material which rotates the plane of polarization of polarized light passing through the material as a function of an applied or developed normal magnetic field.

Figure 1:
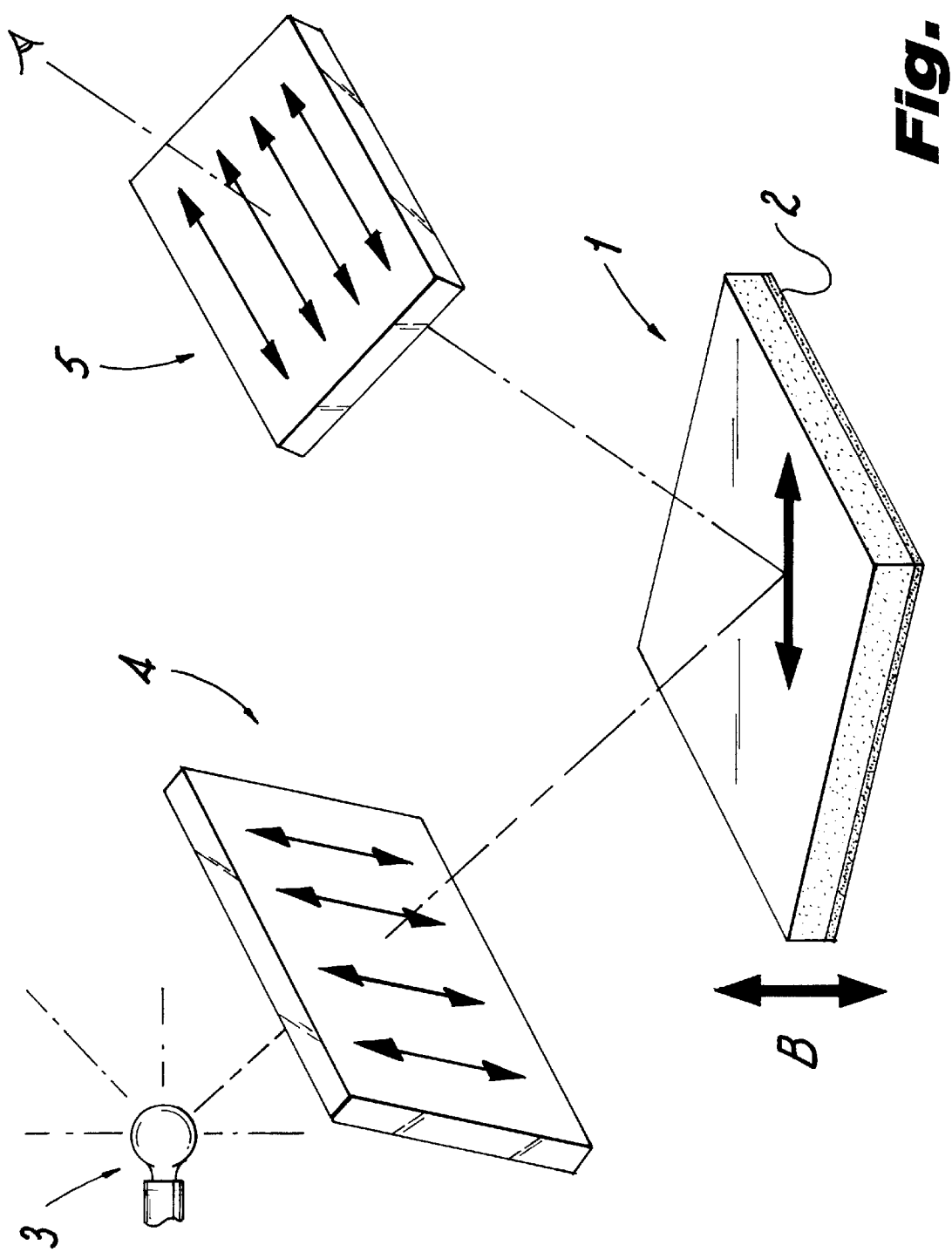
FIG. 1 illustrates a schematic diagram of a conventional Faraday magneto optic effect reflective crystal imaging system, as is well known in the prior art.

Referring to the drawings in detail, FIG. 1 illustrates a schematic diagram of a typical magneto-optic effect sensor which employs a magneto-optic crystal, such as a garnet/iron crystal 1, coated with a dielectric reflective layer 2 which causes light passing through the crystal from a source 3 and polarizer 4 to reflect back through the crystal to a polarization detector 5, as shown in FIG. 1. On each pass of polarized light through the crystal, the initial polarization is rotated in a direction determined by an applied magnetic field B. Although the reflective coating 2 is not essential, by utilizing a double pass configuration, the rotational sensitivity of the sensor is increased by a factor of two.

Such a sensor can be used for non-destructive structural inspections by applying an alternating magnetic field to the structure being tested or inspected. The alternating magnetic field induces a uniform flow of eddy currents in the structure. Pursuant to Lenz's law, the eddy currents in turn create weak secondary magnetic fields which oppose the applied field and are therefore normal to the eddy currents and to the plane of the sensor. The low intensity secondary magnetic fields cause a local rotation of the plane of polarization of the light passing through the sensor. The local rotation of the plane of polarization creates a spatial image on the sensor, which is latent until light passing through the sensor is intercepted by the polarization detector or analyzer which converts variations in polarization to intensity modulation. Any cracks, surfaces, or sub-surface anomalies in the test sample or structure being inspected will disrupt the flow of eddy currents and therefore vary the secondary magnetic fields, with the variations being detected by the magnetic-optic sensor in order to determine the nature and extent of the anomaly.

A disadvantage of conventional systems using the type of sensor shown in FIG. 1 is that when an induced eddy current is parallel to a crack or other anomaly, the level of disturbance available to create the perpendicular secondary magnetic field needed to rotate the local polarization in the magneto-optic crystal, and thereby detect the crack, will be negligible. This increases the susceptibility of the image formed by the sensor to background interferences effects. As a result, conventional magneto-optic measuring instruments must be manually rotated in order to ensure that anomalies in all directions are detected. This slows the inspection process, puts a limitation on miniaturization and the use of automated pattern detection techniques, and makes remote unmanned inspections using magneto-optic technology impossible.

Figure 2:
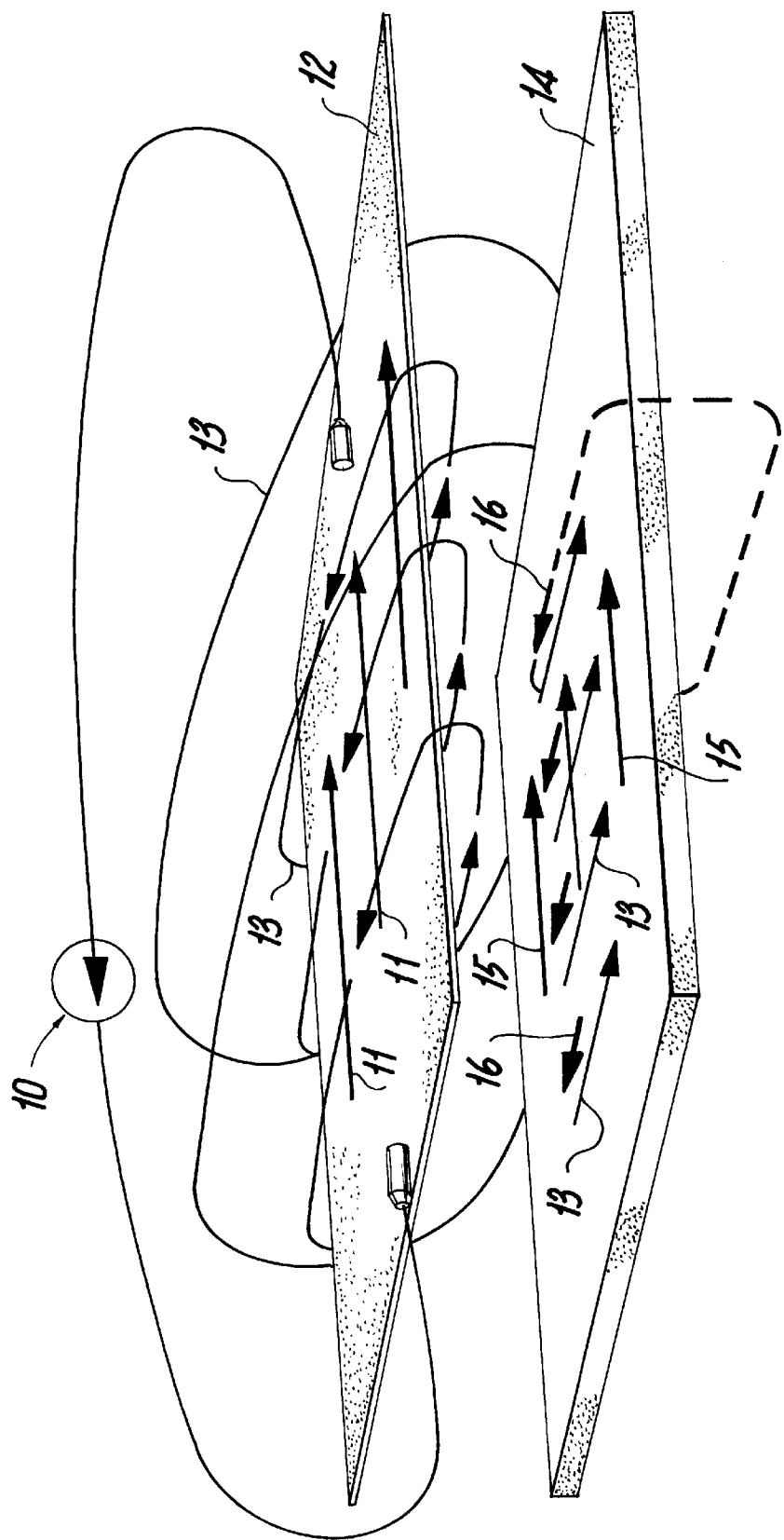
FIG. 2 is a schematic diagram showing the principles which control the arrangement for generating an applied magnetic field used by the present invention, including illustrations of the eddy current and secondary fields resulting from application of the magnetic field to an ideal test sample with no cracks or anomalies of any kind.
Figure 3:
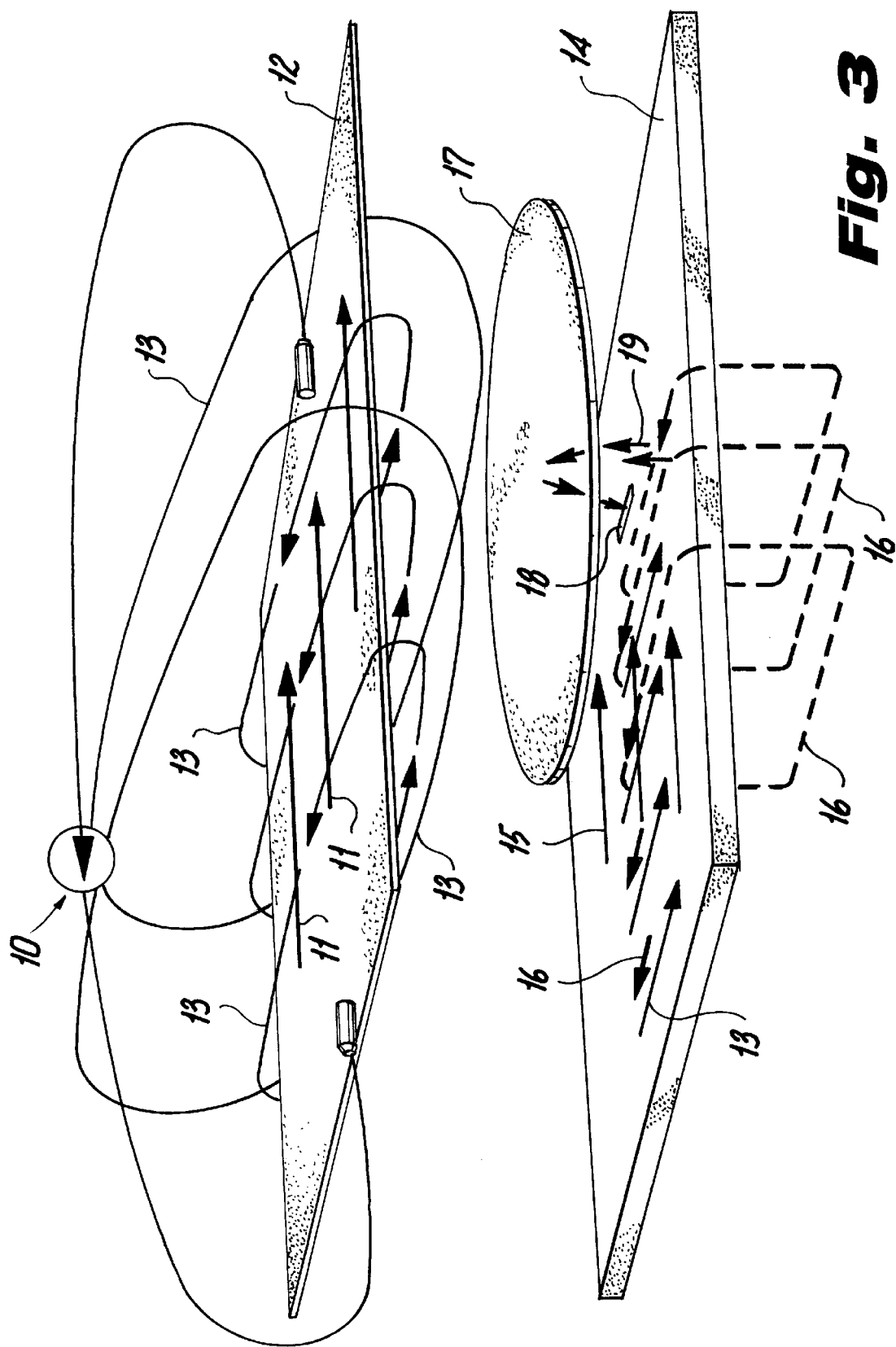
FIG. 3 is a schematic diagram illustrating the manner in which a crack affects the eddy currents and secondary magnetic fields induced by the magnetic field generating arrangement of FIG. 2.

FIGS. 2–3 illustrate the manner in which eddy currents are induced in a non-ferrous test sample or structure by an applied magnetic field. The induced eddy currents behave according to the rule derived from Faraday's law which, in its integral form, states that a voltage drop (emf) must exist about any path that surrounds a time varying change in magnetic flux, as follows:

$$\mathrm{emf} = -\int_S \frac{\partial B}{\partial t} \cdot n\, \mathrm{da}$$

where S is the surface bounded by the closed path around which the emf is induced. If the path in question lies inside the conductor in which the flux is changing, the voltage will induce a current flow to eddy current.

Eddy currents tend to flow around the surface of a conductor in the manner of a sheet solenoid, and in a direction opposite to the inducing flux change. As a result, the H-field of the eddy current is opposite to the applied field. This is the field that intercepts the cracks and other anomalies in the sample.

The relationship between the applied field, induced eddy currents, and resulting secondary fields for a structure with no anomalies is illustrated in FIG. 2. In the illustrated arrangement, an alternating current source 10 causes an alternating sheet current 11 to flow in sheet conductor 12, which is turn generates an alternating primary magnetic field 13 which follows the right hand rule and is at right angles to the current flow. This field passes through the test sample 14 and, in accordance with Faraday's law, induces a voltage drop across the sample 14. The voltage drop causes an eddy current 15 to flow. The eddy current 15 in turn generates a secondary magnetic field 16 which, according to Lenz's law, opposes applied field 13.

As long as the sample is uniform, the secondary magnetic field 16 caused by the eddy current flow takes the form of one large solenoidal magnetic field, as shown in FIG. 2, that couples uniformly into, but not necessarily normal to, the magneto-optic sensor 17 (shown in FIG. 3, but not in FIG. 2). If a crack 18 or other anomaly disrupts the uniform flow of the alternating eddy current, causing it to change its local path in the test sample by flowing around the crack, as shown in FIG. 3, the opposing magnetic field also is disrupted. As the eddy current flows around the crack, a local opposing magnetic field 19 is generated. This opposing magnetic field changes polarity on either side of the crack as the AC eddy current alternates polarity and thus can, in principle, be detected by the sensor. However, in practice, if the crack 18 is very fine and parallel to the flow of the eddy current in the test sample, since there is no impedance to speak of to the current flow, no local disruption of the current occurs. In that case, in order to see that particular crack, using conventional apparatus, the operator must rotate the entire test instrument in order to obtain an eddy current which is normal to the crack. This problem can be avoided by rotating the applied magnetic field relative to the structure being tested or inspected without rotating either the sheet conductor or the sensor.

Figure 4:
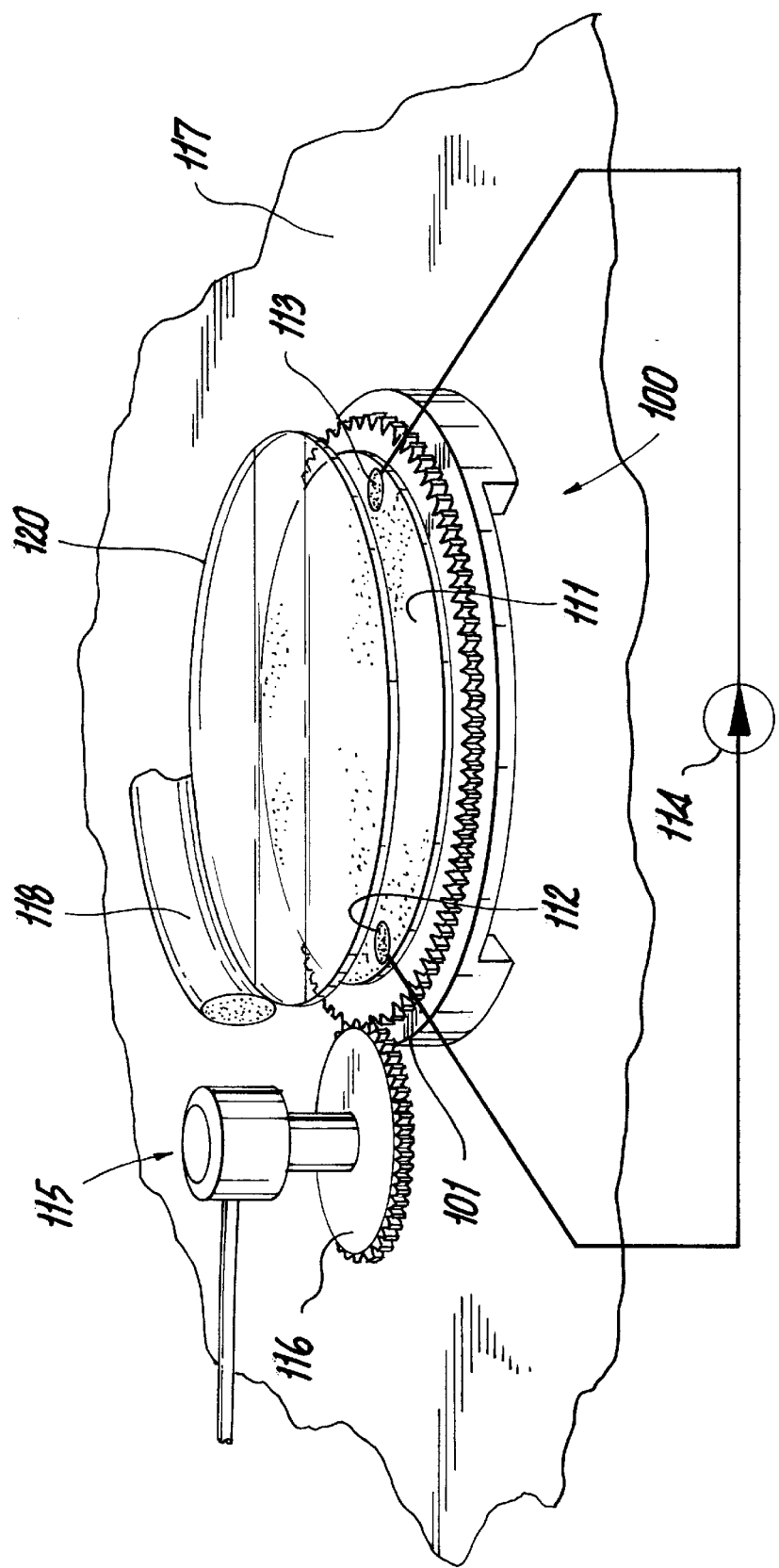
FIG. 4 is a perspective view of a mechanical commutator for rotating a current sheet in a magneto/optic test apparatus in order to rotate an applied magnetic field.
Figure 5:
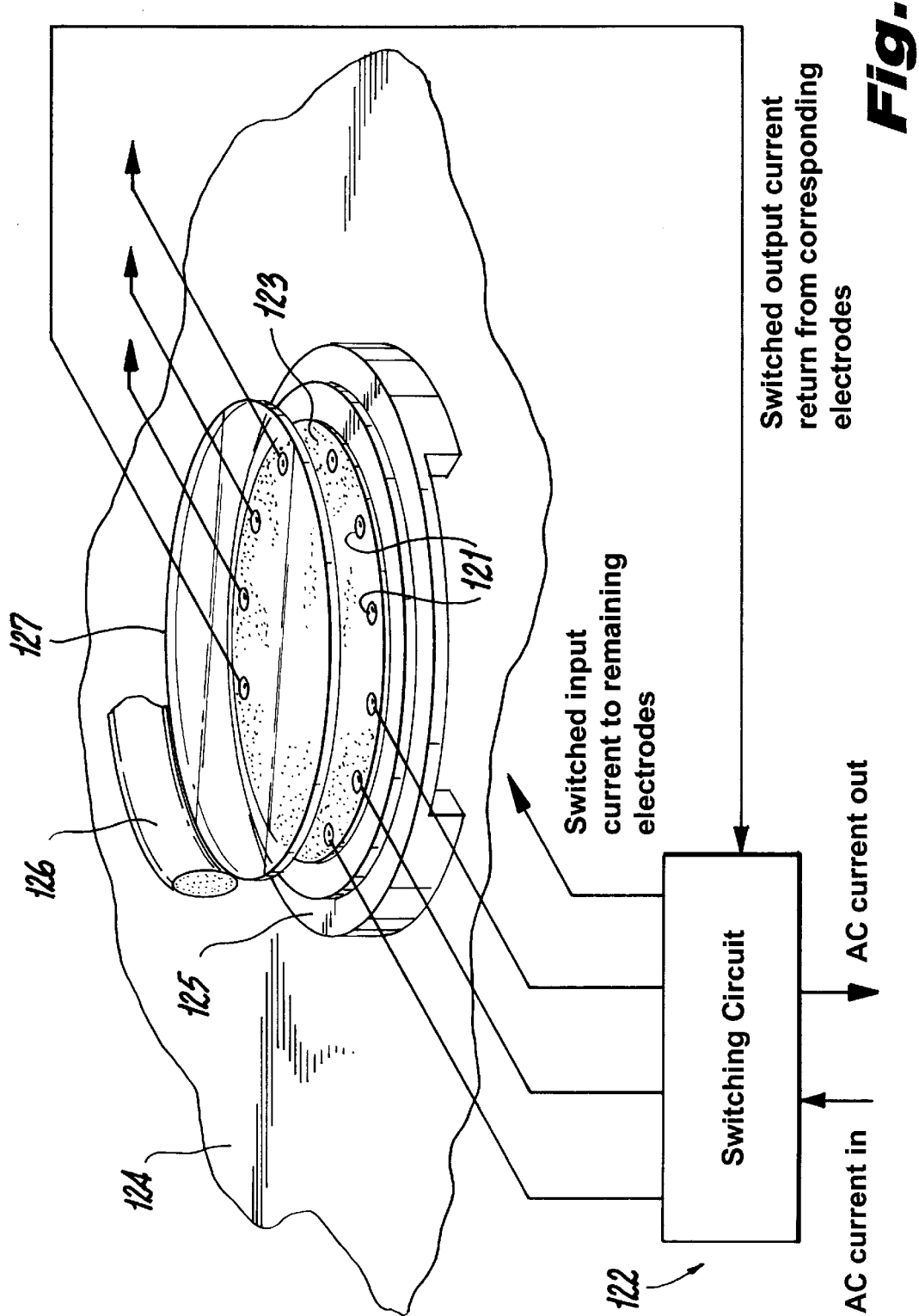
FIG. 5 is a perspective view of an electronic commutator for rotating a current sheet in a magnetic-optic test apparatus in order to rotate an applied magnetic field.

In the first two embodiments illustrated herein in FIGS. 4 and 5, the eddy currents are rotated by changing the direction of sheet currents which generate the applied magnetic field. In the embodiment shown in FIG. 4, a mechanized ring-shaped commutator 100 supported on a bearing structure 101 is arranged to rotate around the perimeter of a thin sheet conductor 111. The commutator 100 carries at least two diametrically opposed electrodes 112 and 113 which are in sliding contact with the conductor 111 so that the electrodes cause a sheet current to flow in the conductor when connected to current source 14. The location at which the diametrically opposed pair of electrodes 112 and 113 contact the conductor 111 determines the direction of the current flow, and the current flow is thus varied as the commutator and electrodes are rotated around the current sheet. The commutator is preferably rotated directly or remotely by a stepper or other electric motor 115 through, for example a gear drive 116.

The test instrument of this embodiment may also include, in addition to the above-described arrangement for applying a primary magnetic field to the test sample or inspected structure 117, by generating a current sheet in conductor 111, an arrangement 118 for applying a permanent bias field to the test sample or structure being inspected, in a manner known to those skilled in the art. Details of the motor, drive and bearing structure will of course be readily filled-in by those skilled in the art and, in addition, those skilled in the are will appreciate that a variety of sensors 120, including the conventional garnet crystal type of sensor, may effectively be employed with the magnetic field rotation apparatus.

An alternate method of rotating the sheet current which generates the applied magnetic field is to electronically commutate the sheet current, as shown in FIG. 5. The electronic commutator includes a set of pairs of diametrically opposed electrodes 121 for each desired current direction and a switching circuit 122 to electronically switch the electrical connections among the array of permanently attached electrodes around the perimeter of the conductor 123 that carries the sheet current. Similar to element 118 in FIG. 4, an arrangement 126 is provided for applying a permanent bias field to the test sample or structure being inspected. As with the embodiment shown in FIG. 4, the flow of current in the sheet conductor 123 produces a normal magnetic field that passes through the structure under test 124. This field in turn produces an eddy current in the structure in a plane parallel to that of the conductor sheet and in a direction which opposes the applied magnetic field. As a result, rotating the current in the sheet conductor 123 rotates the eddy currents in the sample or structure under test 124. As in the example of a mechanical commutator, a support structure for the conductor as well as a biasing arrangement can easily be provided by those skilled in the art, and a variety of sensors 127 can be used to detect the resulting secondary magnetic fields as described above.

Figure 6:
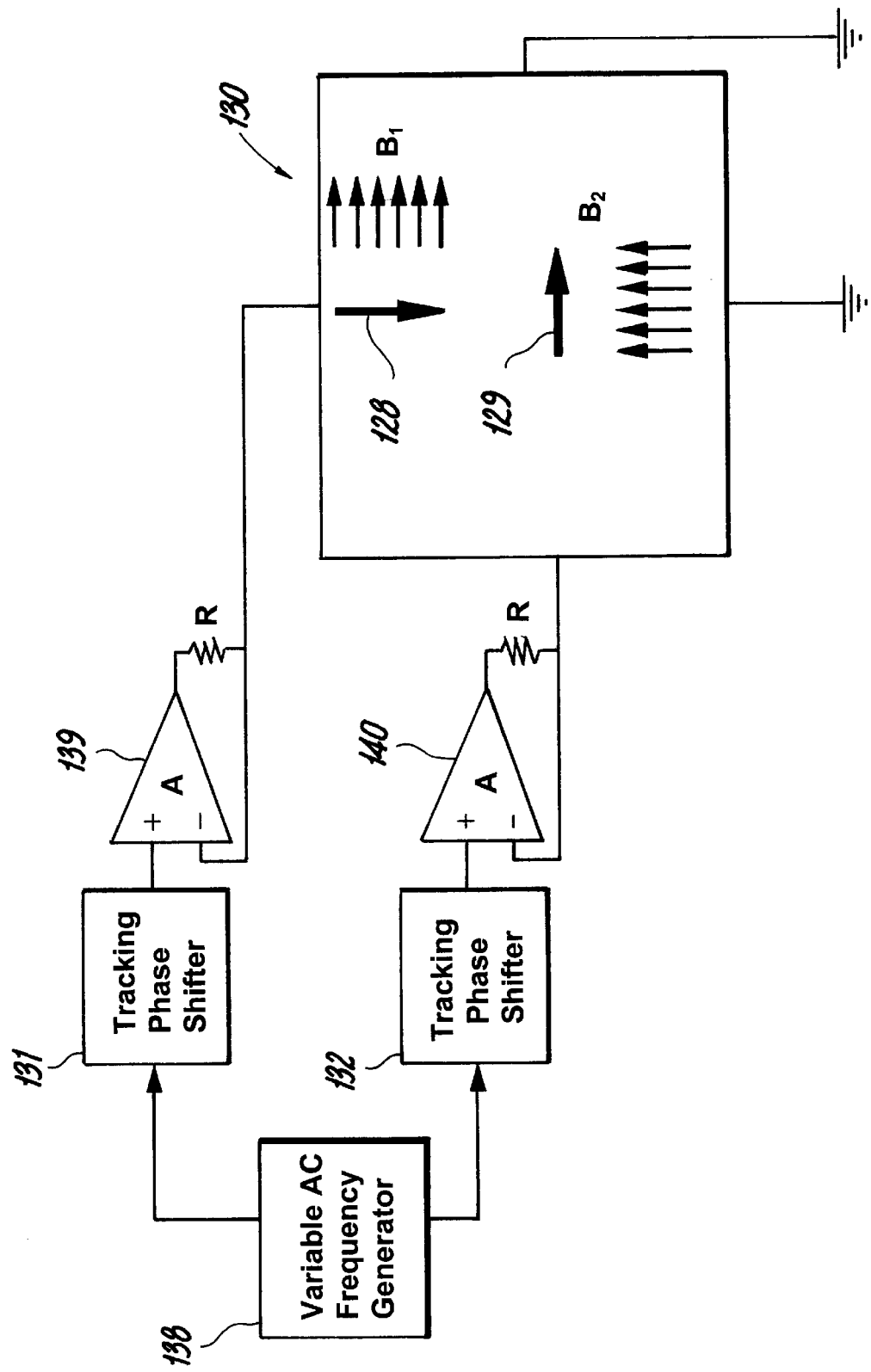
FIG. 6 is a schematic diagram of an arrangement for rotating an applied magnetic field by controlling the phases of multiple current sheets in a magneto-optic test apparatus.

FIG. 6 shows an apparatus and method of eddy current rotation according to a third preferred embodiment. This embodiment involves rotating the resultant magnetic field produced by the interaction of two magnetic fields $B_1$ and $B_2$ generated by independent AC sheet currents 128 and 129 flowing in a thin sheet conductor 130 to obtain the primary applied magnetic field. Rotation of the applied magnetic field is controlled by controlling, using phase shifters 131 and 132, the relative phase difference between the AC current sheets 128 and 129 flowing in the conductor 130. As in the previous two embodiments, the applied magnetic field is caused to pass through a test sample (not shown) to produce an eddy current flow in the plane of the sample in a direction that opposes the flux change of the applied magnetic field. The resulting eddy currents flow in an angular direction in the sample plane which is a direct function of the relative phase between the sheet currents. Since the phase enhanced rotation is frequency sensitive, compensation can be provided by a variable AC generator 138 to ensure that the phase change is proportional to a controlled change independent of frequency. Associated electronic circuits such as comparators 139 and 140 can be used to generate wave shapes which will form various search and track patterns in the sample.

Figure 7:
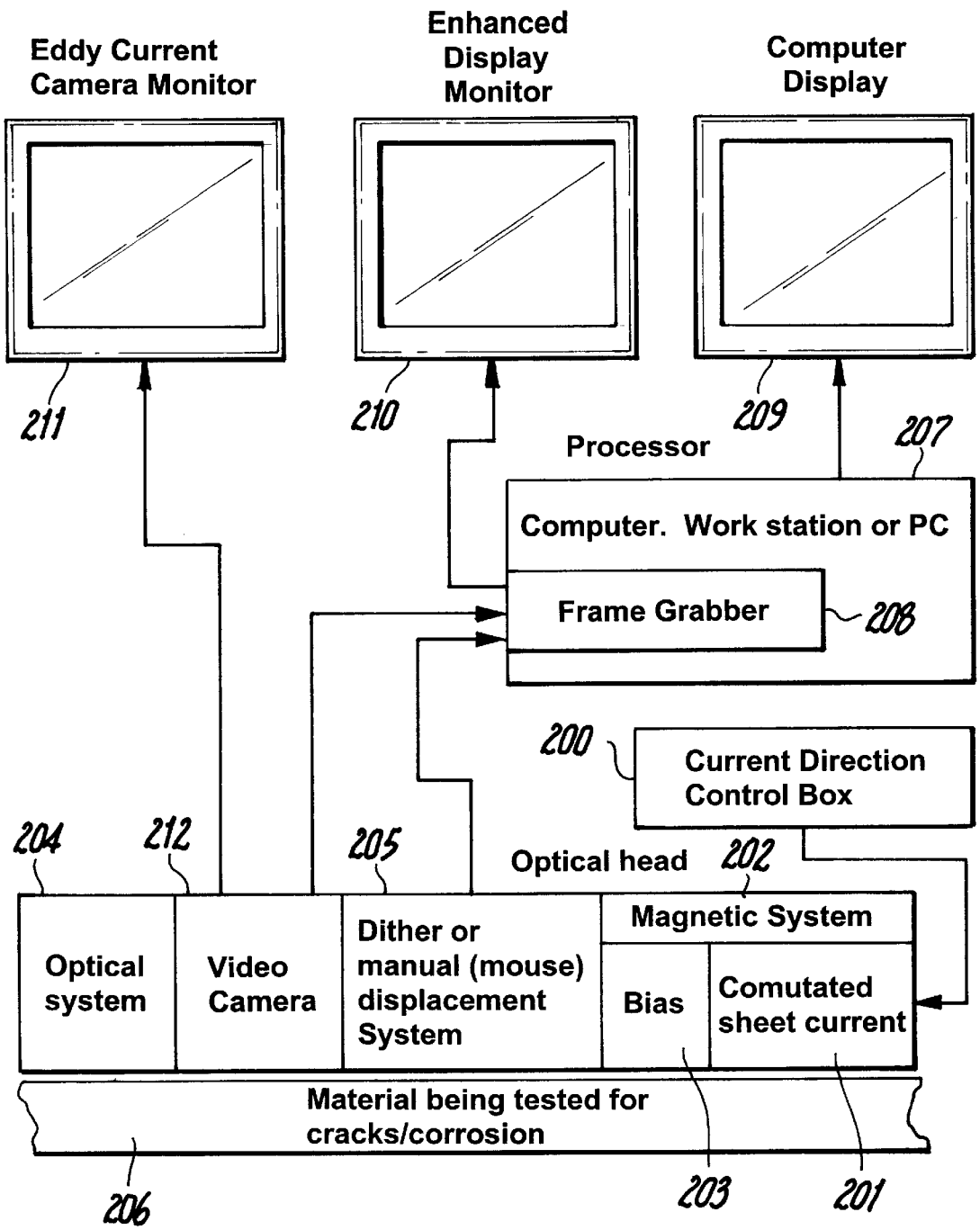
FIG. 7 is a block diagram of a magneto-optic eddy current system background cancellation system and a rotatable current sheet of the type illustrated FIGS. 4–6.

A complete test or inspection system utilizing the preferred sheet current rotating apparatus is shown in FIG. 7. The preferred current rotating apparatus includes a current direction controller 200 which can include either a mechanical or electrical commutation control, or a phase control as described above, for controlling the sheet current 201 in a sheet conductor. The magnetic system 202 may also include a bias magnet 203. The sensor (optical head), optics 204, and other elements of the overall inspection system form no part of the present invention, but it is noted that the inspection system may include a displacement system 205 and/or a dithering system for background cancellation, and also a video camera 212 for allowing the operator to manually guide the sensor and conductor over the sample under test 206 using the displacement system. Because the sensor and magnetic system do not have to be rotated as they are displaced over the structure being inspected, the system can easily be adapted to perform remote unmanned inspections, for example by using robotics to displace the apparatus relative to the test sample.

Control is provided by, for example, a computer, work station, or PC 207 which includes a frame grabber 208, and a monitor 209. In the system shown in FIG. 7, images of the sample under test 206 are displayed on an enhanced display monitor 210 and the output of the magneto-optic sensor is displayed on a separate monitor 211 for visual evaluation. In additional, the improved signal-to-noise or image-to-background ratio of the images enables pattern recognition techniques as described hereinbelow to be employed, permitting completely automated operation of the system.

Figure 8:
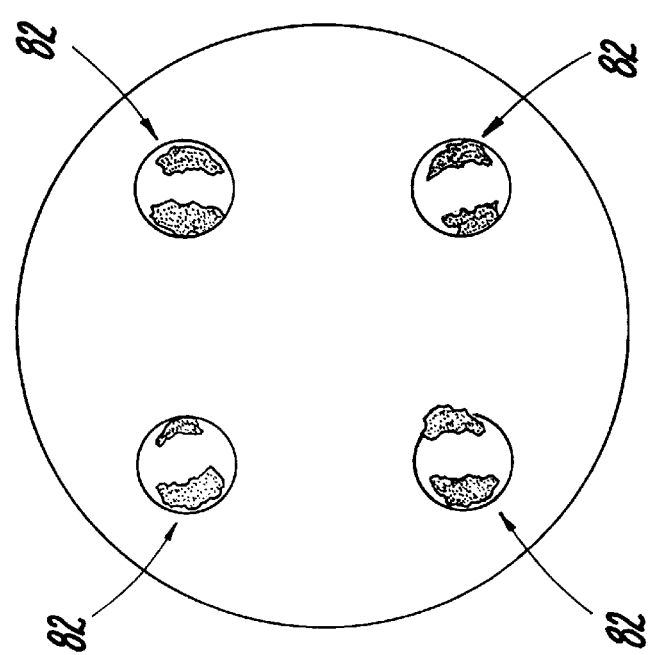
FIG. 8 illustrates a magneto optic image of four drilled bolt holes pursuant to the method of the present invention, which can be examined for the presence of cracks around the drilled bolt holes.

FIG. 8 illustrates a magneto optic image 80 of four drilled bolt holes 82 in a structure which can be subjected to a magneto optic image inspection pursuant to the present invention. A magneto optic image is formed of the circular hole under test, wherein a crack near the circular hole perturbs the circularity of the hole image by driving the magnetic field away from the circumference of the circular hole to cause the image of the hole to appear out of round and eccentric. The present invention applies a pattern recognition analysis to the image to check the image for a circular shape, wherein the circular shape image is correlated with a circle of similar diameter to check the circularity of the image, and an eccentricity of the circular image shape is indicative of a crack around the circular hole.

Figure 9:
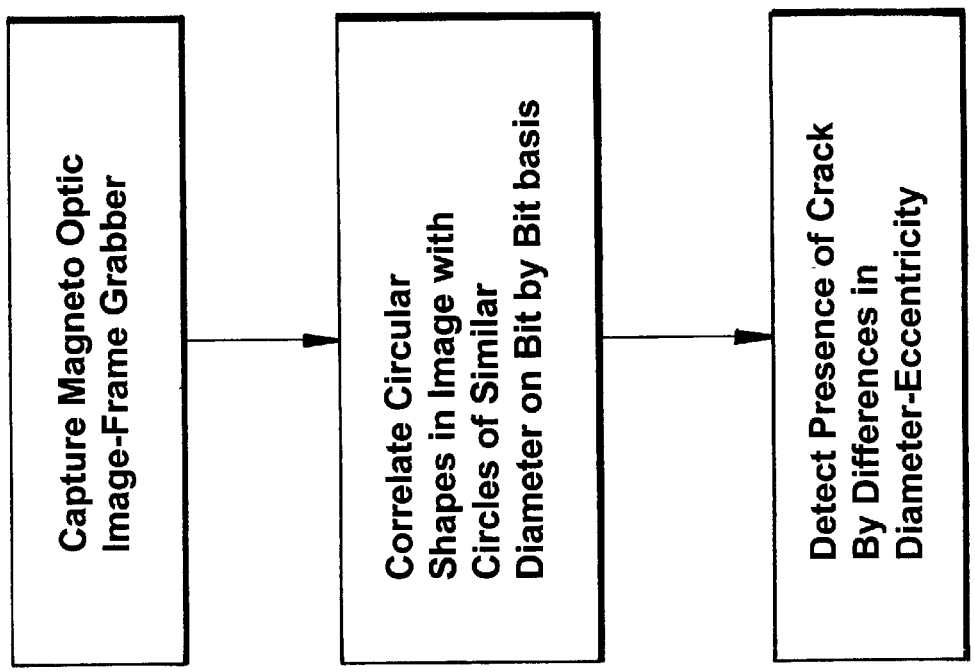
FIG. 9 is a diagram of the pattern recognition analysis in which a circular magneto optic image of a drilled bolt hole is examined and compared on a bit by bit basis with a circle of comparable size to determine any eccentricity in the magneto optic image.

FIG. 9 is a diagram of a pattern recognition analysis in which a circular magneto optic image of a drilled bolt hole is examined and compared on a bit by bit basis with a circle of comparable size to determine any eccentricity in the image. In greater detail, the image in frame grabber 208 is scanned by a pattern recognition program which checks the image for circular image shapes. When a circular image shape is detected in the magneto optic image, it is compared with a circle of similar diameter, and the circularity of the image is determined. In a bit by bit comparison, the pattern recognition program looks for differences in the diameter of the image which can be related to an eccentricity, which in turn is characteristic of a crack around a circular drilled bolt hole. The pattern recognition computer program has a high sensitivity to the slight changes in the image caused by a small crack, thereby achieving a method for locating this phenomenon with relative ease.

The pattern recognition program an be implemented by a pattern recognition program such as the program KHOROS, available from the University of New Mexico. Alternatively, the pattern recognition can be implemented in a pattern recognition neural network, available commercially in software, which has been programmed to analyze the image for noncircular shapes therein.

While several embodiments and variations of the present invention for a magneto optic image feature extraction are described in detail herein, it should be apparent that the disclosure and teachings of the present invention will suggest many alternative designs to those skilled in the art.

What is claimed is:

1. A method of magneto optic imaging to locate the presence of a crack around a circular hole wherein the circular hole, because of its sharp corners, locally disturbs the magnetic field used to form the image and obscures the presence of a crack therearound, comprising:
   a. forming a magneto optic image of a circular hole under test, wherein a crack near the circular hole perturbs the circularity of the hole image by driving the magnetic field away from the circumference of the circular hole to cause the image of the hole to appear out of round and eccentric; and
   b. applying a pattern recognition analysis to the image to check the image for a circular shape, wherein the circular shape image is correlated with a circle of similar diameter to check the circularity of the image, and an eccentricity of the circular image shape is indicative of a crack around the circular hole.

2. A method of magneto optic imaging to locate the presence of a crack around a circular hole as claimed in claim 1, wherein a computer program, in a bit by bit comparison, looks for differences in the diameter of the hole image which can be related to eccentricity, which is characteristic of a crack around the circular hole.

3. A method of magneto optic imaging to locate the presence of a crack around a circular hole as claimed in claim 1, wherein said step of forming a magneto optic image further comprises the steps of:

(a) generating an alternating primary magnetic field, the primary magnetic field in turn inducing eddy currents in a structure under inspection, the eddy currents in turn generating an opposing magnetic field, and including the step of causing a sheet current to flow through a conductor sheet; and (b) rotating the primary magnetic field by controlling the sheet current.

4. A method as claimed in claim 3, wherein the step of controlling the sheet current comprises the step of controlling a direction of the sheet current in the conductor sheet.

5. A method as claimed in claim 4, wherein the step of controlling a direction of the sheet current comprises the step of mechanically commutating the sheet current.

6. A method as claimed in claim 5, wherein the step of mechanically commutating the sheet current comprises the steps of rotating, relative to the conductor sheet, a ring to which at least two electrodes are fixed, the electrodes being in slidable contact with the sheet, and supplying an alternating current to the electrodes and thereby to the sheet, the sheet current flowing between the electrodes so that the orientation of the electrodes relative to the sheet determines the direction of the sheet current.

7. A method as claimed in claim 4, wherein the step of controlling a direction of the sheet current comprises the step of electrically commutating the sheet current.

8. A method as claimed in claim 7, wherein the step of electrically commutating the sheet current comprises the step of selectively applying alternating current to at least one of a plurality of diametrically opposed pairs of electrodes fixedly positioned around the conductor sheet, the position of the at least one pair being supplied with current determining the direction of the sheet current in the conductor sheet.

9. A method as claimed in claim 4, wherein the step of controlling the sheet current comprises the steps of supplying a second sheet current independent from the first sheet current to the conductor sheet and shifting the relative phases of the respective sheet currents.

10. A method as claimed in claim 3, including the step of positioning a magneto-optic sensor relative to the structure under inspection to sense the opposing magnetic field by changing a polarization of polarized light passing through the sensor according to the direction of the opposing magnetic field.

11. A method as claimed in claim 10, further comprising the step of displacing the sensor and conductor sheet relative to the structure under inspection, whereby the sheet current can be rotated as the sensor and conductor sheet are guided across the structure without the need for rotating either the sensor or conductor in order to detect anomalies at any point in the structure.

* * * * *